United States Patent [19]

Kraska et al.

[11] 4,010,760
[45] Mar. 8, 1977

[54] COUPLING ASSEMBLY FOR IMPLANTABLE ELECTROMEDICAL DEVICES

[75] Inventors: Robert E. Kraska, Minneapolis; Pieter M. J. Mulier, St. Paul, both of Minn.

[73] Assignee: Medtronic, Inc., Minneapolis, Minn.

[22] Filed: May 23, 1975

[21] Appl. No.: 580,042

[52] U.S. Cl. .................... 128/419 PS; 128/419 P; 339/94 A; 339/95 B; 339/116 R
[51] Int. Cl.² .................................................. A61N 1/36
[58] Field of Search ...... 128/419 P, 419 PS, 419 R, 128/419 E, 419 C, 421, 422, 1 R; 339/94 A, 95 B, 95 T, 114, 115 C, 115 R, 116 C, 116 R

[56] References Cited
UNITED STATES PATENTS 3,807,411  4/1974  Harris et al. .................. 128/419 P
3,818,304  6/1974  Hursen et al. .................. 128/419 PS

OTHER PUBLICATIONS

Abstract of British Patent No. 1274882, published 5/28/70, p. 654.

*Primary Examiner*—William E. Kamm
*Attorney, Agent, or Firm*—Joseph F. Breimayer; Irving S. Rappaport

[57] ABSTRACT

A body implantable electromedical device such as a cardiac pacemaker in which the stimulating signal generator module is detachably coupled to at least one of the power source modules and the leads, coupling being provided by assemblies which are body fluid corrosion resistant and inhibit current leakage between units of the assembly at different electrical potentials.

14 Claims, 3 Drawing Figures

U.S. Patent  Mar. 8, 1977  4,010,760
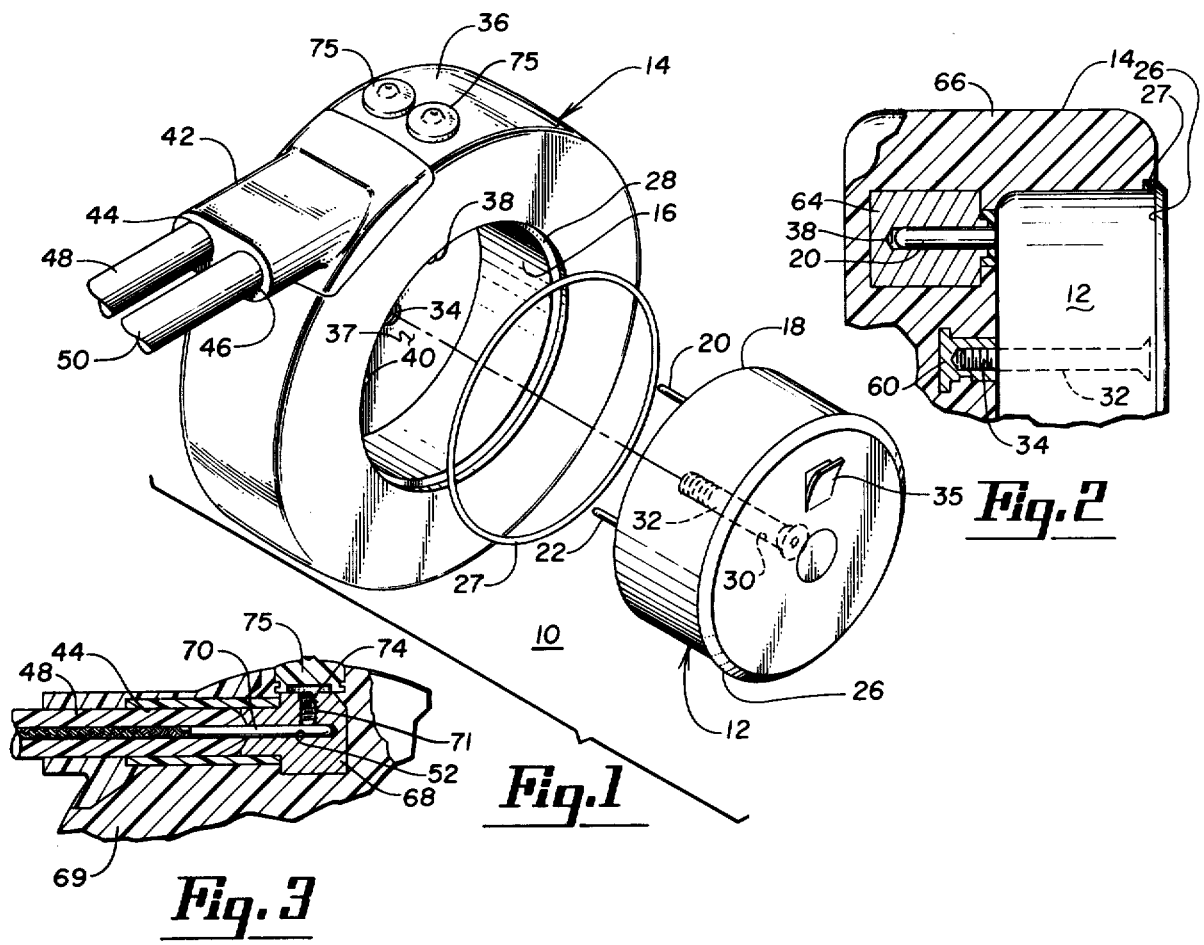

COUPLING ASSEMBLY FOR IMPLANTABLE ELECTROMEDICAL DEVICES

This invention relates to the field of electromedical devices, especially of the body implantable type. In one aspect, it relates to such a device having a replaceable power source. In another aspect, it relates to a coupling mechanism for electrically coupling modules of an implantable electromedical device, which mechanism is chemically resistant to body fluid and inhibits current loss across the members making up such coupling mechanism.

The invention will be particularly described in respect to a cardiac pacemaker; however, it is to be understood that the invention has general application to implantable electromedical devices.

STATE OF THE ART

Implantable electromedical devices such as cardiac pacemakers have been known and commercially used for many years. Such devices have an integral power supply module and an electronic circuitry module, and stimulating pulse conducting leads from the device proper to the tissue or organ to be stimulated.

SUMMARY OF THE INVENTION

Upon depletion of the power supply below an acceptable level, the entire device less the leads must be removed in its entirety and replaced by another composite (integral power module/electronic circuit module) device, notwithstanding the fact that only the power supply module actually requires replacement. It would be desirable from the standpoint of the patient's well-being as well as from an economic standpoint to leave the electronic circuit module in tact and replace only the power supply module.

One major problem to be overcome in providing a body implantable device with a separately attachable power supply is that created by the presence of body fluid. Body fluid, which is an electrolyte, will infiltrate between the power supply and pulse generator or electronic circuit module, providing both a corrosive environment for exposed surfaces of the coupling assembly and an electrically conductive path between adjacent oppositely polarized electrically conductively mated units of the coupling assembly. Since these adjacent units of the coupling assembly are at different electrical potentials, current leakage may occur across the intervening electrolytic path provided by the body fluid, resulting in a drain on the power supply.

It is an object of this invention to provide an implantable electromedical device having a replaceable power supply. Another object is to provide a coupling assembly for electrically coupling components of an implantable electromedical device which resists corrosion from body fluid and inhibits current loss between adjacent units thereof at different electrical potentials.

In accordance with the above, there is provided a body implantable electromedical device comprising electrical potential source means, generating means for generating a stimulator signal, lead means for transmitting said signals to a remote situs, and a coupling assembly for detachably coupling said electrical potential source means to said generator means, said coupling assembly providing a coupling of said electrical potential source means to said generator means which is resistant to chemical degradation by body fluid and further which allows the flow of electrical current to said generator means without substantial current loss.

In a preferred embodiment, the coupling assembly comprises at least first and second electrically couplable units each comprising first and second means, said first unit being adapted to be at a higher electrical potential than said second unit, at least said first and second means of said first unit being composed of a material having an electrochemical breakdown potential in excess of the electrical potential provided by said electrical potential source means and further having a passive current density such that the leakage current between said electrically couplable units is substantially less than the current demand of the stimulator signal emitting unit

BRIEF DESCRIPTION OF THE DRAWINGS

The invention will be described with reference to the attached drawings wherein:

FIG. 1 is a pictorial view of an implantable device of this invention with the signal emitting and power supply units separated to show the coupling mechanism;

FIG. 2 is a sectional view of the coupling assembly for the signal emitting and power supply units; and FIG. 3 is a sectional view of the coupling assembly for the signal emitting and lead units.

DESCRIPTION OF THE PREFERRED EMBODIMENTS

Referring to FIG. 1, an implantable bipolar demand pacemaker 10 is depicted composed of a power supply module 12 and a stimulator signal emitting module 14. The module 12 is cylindrically shaped to slide into cavity 16 of module 14. Extending outwardly from face 18 of module 12 and perpendicular thereto are cylindrically shaped male pins 20 and 22. The pins are electrically connected to the power source (not shown) located within module 12; pin 20 being connected to the positive terminal and pin 22 being connected to the negative terminal of the power supply. Preferably, the pins are widely separated on face 18 to provide a secure coupling to module 14. Module 12 is provided with a lip 26 and o-ring 27 which fits into complementary-shaped recess 28 in module 14. Module 12 is also provided with a central bore 30 for receiving threaded screw 32. Cavity 16 of module 14 has a threaded bore 34 in alignment with bore 30 for receiving screw 32 thereby detachably connecting modules 12 and 14. Located on the face of module 12 opposing face 18 is a recessed tab 35 to facilitate gripping and removal of the module 12 from connection with module 14.

Signal emitting module 14 includes housing 36 containing the electronic circuitry for converting the power supplied by module 12 to a suitable stimulating signal as is known in the art. Suitable circuitry includes the circuitry for producing a demand pulse for heart pacemakers, such as Medtronic Module 5942 Implantable Bipolar Demand Pulse Generator. Located in face 37 of cavity 16 are a pair of female receptacles 38 and 40 of a size adapted to receive male pins 20 and 22. Housing 36 also includes a boot 42 providing a pair of apertures 44 and 46 for receiving conventional electrical leads 48 and 50, respectively. Apertures 44 and 46 communicate with a second set of female receptacles, one of which is shown as 52 in FIG. 3.

FIG. 2 illustrates the mating of the modules 12 and 14. Screw 32 is positioned in threaded bore 34 which in turn is drilled in metal block 60. Screw 32 is inset slightly and the recess so provided is filled with a biocompatible, electrically insulating resin filler. Pin 20, positioned in receptacle 38 tapped in metal block 64 constitutes one electrically couplable unit. Receptacle 40 is located in a similar block for positioning pin 22, thereby providing a second electrically couplable unit. Blocks 60 and 64 (as well as the block for pin 22) are set in a transparent, electrically insulating biocompatible resin encapsulant 66. An epoxy resin has proved suitable. Pin 20 and receptacle 38 (as well as pin 22 and receptacle 40) should be of such relative size that good electrical contact is provided between the coupled or mated elements. As will be explained hereinafter, the fit of the elements of the electrically couplable units should result in removal of an electrical insulating coating or surface on at least portions of the mated parts of such couplable unit. A frictional fit of the pin in the receptacle will provide this result.

FIG. 3 illustrates the coupling assembly for coupling the electrical leads 48 and 50 to the pulse generator module 14. Only coupling of lead 48 is shown; the coupling of lead 50 being the same. The female receptacle 52 is located in metal block 68 encapsulated in an epoxy resin 69. The lead terminal 70 of lead 48 is held in place by metal setscrew 74 of the Allen type located in threaded aperture 71 of block 68. The lead terminal of lead 50 (not shown) is coupled in the same manner. Setscrew 74 is turned down onto lead terminal 70 such that at least a portion of the electrical insulating coating on the couplable units is removed to provide good electrical contact between the setscrew 74 and the terminal 70. Covering set screw 74 is a self-healing, biocompatible, electrically insulating resin 75. This resin may be punctured by an Allen wrench to engage setscrew 74. Upon removal of the wrench, the resin reseals.

It is understood that in the embodiments of the invention wherein the circuit module 14 remains implanted, there is no necessity for providing a detachable connection between the leads and the circuit module 14, but such a feature is desirable.

In the case of the power module/circuit module combination, the coupling assembly constitutes a couplable unit comprised of pin 20 and the blocks providing the female receptacle 38 and a couplable unit comprised of pin 22 and the blocks providing the female receptacle 40. In the case of the leads/circuit module combination, the coupling assembly constitutes a couplable unit comprising lead terminal 70, block 68 and setscrew 74 and another couplable unit comprising the lead terminal for lead 50 and a block and setscrew identical to the block 68 and setscrew 74, respectively.

At least one and preferably both of the coupling units are composed of an electrical volume conductor material having surface properties making it biocompatible, body fluid corrosion resistant and electrochemically insulating to direct current. Materials meeting these specifications include niobium, tantalum and titanium, and alloys of the foregoing which will form complete substitutional solid solutions, including (1) tantalum based alloys such as Ta/Ti, Ta/W, Ta/Nb, Ta/Mo; (2) niobium based alloys such as Nb/Ti, Nb/Ta, Nb/W, Nb/Mo; and (3) titanium based alloys such as Ti/Ta, Ti/Nb, Ti/Zr, Ti/Mo. The foregoing alloys form substitutional solid solutions for all ratios of component atoms. These metals have electrical resistivities in the range of 10 to 100 micro ohms-cm. In addition, the above-listed base metals (Ta, Ti, Nb) will form solid solutions when alloyed with minor amounts of numerous other atoms, e.g., niobium alloyed with about 2% or less by weight aluminum.

The metals used in one or both of the coupling units should exhibit an electrochemical breakdown potential in excess of the electrical potential to be applied to the stimulator signal emitting module 14 and a relatively low electrochemical passive current density such that the leakage current is substantially less than the current demand of the signal emitting module 14, preferably less than 2% and most preferably less than 1% of the current demand. The above-mentioned metals all have breakdown potentials greater than 5 volts and passive current densities of less than 1 microamp per square centimeter of coupling unit exposed to electrolyte. The voltage range for current heart pacemaker power supply is 2–6 volts. Future implantable devices may have power supplies which provide operating voltages or stimulating signals greater than that for presently known pacemakers.

The surface properties of the coupling unit components referred to above are provided by an oxide coating. The oxide coating is formed naturally in the presence of oxygen. The thickness of the naturally occurring surface oxide is enhanced by a variety of well-known anodization procedures, one of which is described in detail in the following examples. The oxide coating is relatively uniformly distributed and adherent. Further, on a microscopic level the surface is generally composed of peaks and valleys. The coating is removable at these peaks by a scraping or shearing action such as is encountered in connecting the leads to the circuit module or the circuit module to the power supply module to expose the underlying electrically conductive metal. The metal-to-metal contact occurring at these peaks results in a cold weld which establishes a low electrical resistance path for current flow. The coating is, however, self-healing in the sense that if removed, the coating will reform unless oxygen is excluded from the area. Thus, a previously removed coating will reappear in the metals noted above if immersed in body fluid owning to the oxygen in the body fluid and the applied anodic potential. However, where two metals are forced in intimate engagement, the coating is removed at the sites of engagement and the so mated surfaces will be effectively excluded from any environment which will allow reformation of the insulating coating. Accordingly, an electrically conductive path is formed between the mated surfaces.

The above-described oxide-coated metals employed in the coupling units of this invention not only resist chemical corrosion from body fluids which infiltrate the coupling units, but also inhibit short circuiting leakage currents between oppositely polarized units when such body fluid is present. In the absence of such current drain inhibition, current drainage occurs at such a level as to reduce significantly the useful life of the pacemaker or other electrochemical device.

Leakage current is the product of the passive current density ($I_p$) and the surface area (A) of the coupling unit exposed to body fluid or other electrolyte ($I_1 = I_p \times A$). Leakage current may be minimized by minimizing $I_p$ or A, but there is a severe limitation on how far A can be reduced while retaining the requisite mechanical properties for the connector assembly. Thus, the best way to limit $I_1$ is to limit $I_p$, which effectively also minimizes the corrosion rate of the coupling members since corrosion rate is theoretically proportional to $I_p$.

A typical area for the coupling unit is in the range of 0.5 to 7.5 cm$^2$, generally, 1 to 4 cm$^2$. The surface area referred to above is the original area of the coupling unit less the total contact surface area (the areas where the cold welds occur). The latter may be disregarded as it is quite small compared to the former (original area), since mating occurs on a microscopic level.

Leakage current is minimized when the current is drained from the power source in a direct current mode because the electrochemical impedance of the couplable unit is maximized under pure direct current conditions. With an A.C. signal, as the frequency increases, the electrochemical impedance decreases due to the nonfaradic charge transfer resulting in greater leakage current. Accordingly, at some frequency, the leakage current, even though reduced by the present invention, would be at an unacceptable absolute value.

EXAMPLE 1

Each of the metals shown in Table 1 is anodized in accordance with the following procedure. The metal to be tested is first mechanically polished with 600 grit sandpaper to smooth the surface. After sanding, the metal is immersed in an acid-etch solution to obtain a fresh, contaminant-free surface. The metal is then rinsed to remove etchant residues and then anodized in a saturated solution of sodium ammonium phosphate at 30 volts D.C. for 20 seconds. Each of the anodized metal samples is then employed as the working electrode to determine potentiostatic passive current density in accordance with ASTM G5-71 employing a pseudo-extracellular fluid simulating the relevant chemistry of body fluid. The fluid has a pH of 7.4, and a chloride ion concentration of 0.103 moles/liter. The current density is determined at a single applied potential of +6.0 volts versus saturated calomel electrode. A second set of metals is sanded, etched, and rinsed and exposed to air long enough to acquire a naturally-occurring oxide coating. These metals were also tested according to ASTM G5-71.

Table 1

| Metal | Current Density at Equilibrium (microamps/cm$^2$) | |
|---|---|---|
| | Anodized | Unanodized |
| Niobium | 0.07 | 2.24 |
| Niobium/44 wt.% Titanium | 0.022 | 0.030 |
| Tantalum | 0.0066 | 0.168 |
| Tantalum/10 wt. % Tungsten | 0.0004 | 0.0133 |
| Titanium | 0.0078 | 2.53 |

EXAMPLE 2

A sample of titanium is treated and anodized as described in Example 1 and tested as the working electrode in accordance with ASTM G5-71 to determine potentiodynamic current density at the applied potentials shown in Table 2. A second sample is treated as provided in Example 1 except for the anodization step. This unanodized sample acquires a naturally occurring coating of oxide almost instantaneously. The unanodized sample bearing the naturally occurring oxide coating is tested in the same manner as the anodized sample.

Table 2

| Volts (+) vs. S.C.E. | i/i$_a$ | Current Density (i$_a$) (microamps/cm$^2$) | |
|---|---|---|---|
| | | Anodized (i$_a$) | Nonanodized (i) |
| 0 | 39.8 | 7.60 × 10$^{-4}$ | 3.03 × 10$^{-2}$ |
| 0.2 | 50.5 | 1.20 × 10$^{-3}$ | 6.06 × 10$^{-2}$ |
| 0.3 | 65.5 | 1.55 × 10$^{-3}$ | 1.01 × 10$^{-1}$ |
| 0.5 | 129 | 2.35 × 10$^{-3}$ | 3.03 × 10$^{-2}$ |
| 1.0 | 289 | 4.35 × 10$^{-3}$ | 1.26 |
| 2.0 | 88.7 | 1.42 × 10$^{-2}$ | 1.26 |
| 3.0 | 122 | 1.90 × 10$^{-2}$ | 2.32 |
| 4.0 | 166 | 3.40 × 10$^{-2}$ | 5.65 |
| 5.0 | 218 | 4.35 × 10$^{-2}$ | 9.49 |
| 6.0 | 259 | 5.85 × 10$^{-2}$ | 15.15 |
| 7.0 | 194 | 1.20 × 10$^{-1}$ | 23.23 |
| 7.7 | 288 | 9.80 × 10$^{-2}$ | 28.28 |

It will be understood that the teachings of the present invention may be applied to unipolar pacemaker designs as well as variations on the bipolar pacemaker designs depicted for purposes of illustration in the drawings.

It should be further understood, of course, that the foregoing disclosure relates only to the best modes and only to the inventor of many possible modes of practicing the invention, and that numerous modifications may be made therein without departing from spirit and scope of the invention as set forth in the appended claims.

What is claimed is:

1. A body implantable electromedical device of the type having electrical potential source means for developing a predetermined potential and an electrical current, generating means adapted to receive and responsive to the current from said potential source means for generating a tissue stimulating signal, lead means adapted to be coupled with said generating means for transmitting said signal to a remote situs, and at least one coupling assembly for detachably coupling said electrical potential source means to said generating means comprising at least first and second electrically couplable units each comprising first and second members, said first unit being adapted to be at a higher electrical potential than said second unit, at least said first and second members of said first unit being composed of a material having an electrochemical breakdown potential in excess of the electrical potential provided by said electrical potential source means and further having a passive current density such that the leakage current between said first and second electrically couplable units is substantially less than the current demand of said generating means.

2. The device of claim 1 further comprising a second coupling assembly, said first coupling assembly coupling said electrical potential source means and said generating means, and said second coupling assembly coupling said generating means and said lead means.

3. The device of claim 2 wherein said first members of said first and second couplable units are detachable from said second members whereby said lead means is separable as a unit from said generating means.

4. The device of claim 1 wherein said first members of said first and second couplable units are detachable from said second members whereby said electrical potential source means is separable as a unit from said generating means.

5. The device of claim 1 wherein said leakage current is no more than about 2% of the current demand of said generating means.

6. The device of claim 1 wherein said device is a cardiac pacemaker.

7. The device of claim 1 wherein said first and second members are composed of a metal comprising titanium.

8. The device of claim 1 wherein said first and second members are composed of a metal comprising niobium.

9. The device of claim 1 wherein said first and second members are composed of a metal comprising tantalum.

10. The device of claim 1 wherein said first and second members are comprised of a selected metal having an electrically insulating anodized surface.

11. The device of claim 10 wherein said first and second couplable units comprise means for removing contacting anodized surfaces of said first and second members for establishing a low impedance electrical attachment therebetween.

12. The device of claim 1 wherein said first members are in male, pin form, and said second members are in female, receptacle form, said generating means comprises a pulse generator circuit module having said second members spaced from one another a predetermined distance on a surface of said circuit module, and said electrical potential source means comprises a power source module bearing said first members spaced from one another a corresponding predetermined distance on a surface of said power source module.

13. The device of claim 12 wherein said first and second members are comprised of a selected metal having an electrically insulating anodized surface.

14. The device of claim 13 wherein said first and second couplable units comprise means for removing contacting anodized surfaces of said first and second members for establishing a low impedance electrical attachment therebetween.

* * * * *